(12) United States Patent
Cully et al.

(10) Patent No.: US 7,914,568 B2
(45) Date of Patent: Mar. 29, 2011

(54) BILIARY STENT-GRAFT

(75) Inventors: Edward H Cully, Flagstaff, AZ (US);
Erin B Hutchinson, Parks, AZ (US);
Michael C Nilson, Flagstaff, AZ (US);
Ricardo A Rivera, Tucson, AZ (US)

(73) Assignee: Gore Enterprise Holdings, Inc.,
Newark, DE (US)

( * ) Notice: Subject to any disclaimer, the term of this patent is extended or adjusted under 35 U.S.C. 154(b) by 1322 days.

(21) Appl. No.: 10/907,067

(22) Filed: Mar. 18, 2005

(65) Prior Publication Data

US 2005/0154448 A1 Jul. 14, 2005

Related U.S. Application Data

(63) Continuation of application No. 09/488,229, filed on Jan. 20, 2000, now abandoned, which is a continuation-in-part of application No. 09/235,460, filed on Jan. 22, 1999, now abandoned.

(51) Int. Cl.
*A61F 2/06* (2006.01)
*A61M 29/00* (2006.01)

(52) U.S. Cl. ...................................... 623/1.13; 623/1.44

(58) Field of Classification Search ................. 623/1.11, 623/1.12, 1.13, 1.14, 1.15, 1.17, 1.18, 1.19–1.21, 623/1.44–1.16; 606/108, 191, 194, 195
See application file for complete search history.

(56) References Cited

U.S. PATENT DOCUMENTS

| | | |
|---|---|---|
| 3,657,744 A | 4/1972 | Ersek |
| 3,953,566 A | 4/1976 | Gore |
| 4,187,390 A | 2/1980 | Gore |
| 4,562,596 A | 1/1986 | Kornberg |
| 4,762,128 A | 8/1988 | Rosenbluth |
| 4,893,623 A | 1/1990 | Rosenbluth |
| 5,019,090 A | 5/1991 | Pinchuk |
| 5,123,917 A | 6/1992 | Lee |
| 5,282,823 A | 2/1994 | Schwartz et al. |
| 5,282,860 A | 2/1994 | Matsuno et al. |
| 5,304,200 A | 4/1994 | Spaulding |
| 5,314,472 A | 5/1994 | Fontaine |
| 5,389,106 A | 2/1995 | Tower |

(Continued)

FOREIGN PATENT DOCUMENTS

EP 689 805 1/1996

(Continued)

OTHER PUBLICATIONS

Lammer J et al. Common Bile Duct Obstruction Due to Malignancy: Treatment with Plastic versus Metal Stents. Radiology 1996; 201:167-172.

(Continued)

*Primary Examiner* — Vy Q Bui
(74) *Attorney, Agent, or Firm* — Wayne D. House

(57) ABSTRACT

A stent-graft which is particularly useful for applications in biliary ducts. An expandable stent is provided with a covering of a material which is substantially impervious to body fluids and tissue ingrowth and has an increased resistance to bacterial attachment due to its lack of porosity and reduced surface texture. A preferred covering is porous PTFE film rendered substantially non-porous by a coating of a polymeric material such as FEP. The resulting stent has a thin wall for minimum pre-deployment diameter and for minimum interference with fluid flow through the device after implantation. It has good flexibility, allowing its use in curved ducts.

45 Claims, 9 Drawing Sheets

U.S. PATENT DOCUMENTS

| | | | |
|---|---|---|---|
| 5,474,563 A | 12/1995 | Myler et al. | |
| 5,549,663 A | 8/1996 | Cottone, Jr. | |
| 5,562,697 A | 10/1996 | Christiansen | |
| 5,562,726 A | 10/1996 | Chuter | |
| 5,591,226 A | 1/1997 | Trerotola et al. | |
| 5,591,230 A | 1/1997 | Horn et al. | |
| 5,628,783 A | 5/1997 | Quiachon et al. | |
| 5,662,700 A | 9/1997 | Lazarus | |
| 5,662,713 A | 9/1997 | Andersen et al. | |
| 5,667,523 A | 9/1997 | Bynon et al. | |
| 5,669,936 A | 9/1997 | Lazarus | |
| 5,674,241 A | 10/1997 | Bley et al. | |
| 5,676,696 A | 10/1997 | Marcade | |
| 5,728,158 A | 3/1998 | Lau et al. | |
| 5,735,892 A | 4/1998 | Myers et al. | |
| 5,735,893 A * | 4/1998 | Lau et al. | 623/1.16 |
| 5,755,774 A | 5/1998 | Pinchuk | |
| 5,795,319 A | 8/1998 | Ali | |
| 6,156,064 A * | 12/2000 | Chouinard | 623/1.44 |
| 6,352,561 B1 * | 3/2002 | Leopold et al. | 623/1.23 |

FOREIGN PATENT DOCUMENTS

| | | |
|---|---|---|
| WO | 9721403 | 6/1997 |
| WO | 9827894 | 7/1998 |

OTHER PUBLICATIONS

Pereiras RV et al. Relief of Malignant Obstructive Jaundice by Percutaneous Insertion of a Permanent Prosthesis in the Biliary Tree. Annals of Internal Medicine 1978; 89 (5):589-593.

Pollock TW et al. Percutaneous Decompression of Benign and Malignant Biliary Obstruction. Arch Surg 1979; 114:148-151.

Sze DY et al. Recurrent TIPS Failure Associated with Biliary Fistulae: Treatment with PTFE-Covered Stents. Cardiovasc Intervent Radiol 1999; 22:298-304.

Saito et al. Biliary Endoprosthesis Using GORE-TEX Covered Expandable Metallic Stents. Nippon Acta Radiologica 1994; 54:180-182.

* cited by examiner

BILIARY STENT-GRAFT

CROSS REFERENCE TO RELATED APPLICATIONS

This application is a Continuation of U.S. patent application Ser. No. 09/488,229 filed Jan. 20, 2000, which is a Continuation-in-Part of U.S. patent application Ser. No. 09/235,460 filed Jan. 22, 1999, now abandoned.

FIELD OF THE INVENTION

The present invention relates to the field of implantable stent devices including stents and stent-grafts intended to support the luminal walls of a body conduit, and particularly to biliary stent devices useful for supporting the luminal walls of biliary ducts.

BACKGROUND

The bile duct presents a difficult environment for stent devices implanted within the duct for the purpose of helping the duct to remain patent. Biliary stenting is most commonly performed using lengths of relatively rigid plastic tubing, primarily tubing of non-porous polytetrafluoroethylene or polyethylene. Plastic stent devices used for these applications are less than ideal in that they are known to be subject to occlusion, due to bacterial colonization and build up of biofilm on the luminal surface. Plastic stents are also known to migrate away from their originally implanted location. Further, because of their relatively rigid form, these prior devices do not lend themselves to being provided at a smaller diameter for insertion and for subsequent diametrical expansion during deployment for fitting against the walls of a body conduit such as a bile duct. Metal biliary stents, which have gained increased acceptance over the last decade, are typically balloon expandable or self expanding and are made from various metals including stainless steel and nitinol. Metallic biliary stents have the advantage of being delivered in a low profile, small diameter configuration and deployed in situ to a larger functional diameter appropriate to support the luminal wall of a biliary duct. Due to their larger functional diameters, the patency achieved with metal stents is longer than that of plastic stents; however, metal stents are known to be subject to occlusion from tumor ingrowth through the stent interstices.

SUMMARY OF THE INVENTION

The present invention relates to an implantable stent provided with a covering, also referred to as a stent-graft or more generally as an endoprosthesis, useful for supporting the walls of body conduits in order to aid in maintaining the patency of the supported body conduit. Stent devices generally include stents without covers and having open interstices between adjacent structural elements of the stent (such as adjacent struts), and stents provided with tubular coverings which cover some or all of the stent interstices. The stent coverings described herein may be present on the luminal surface of the stent, the exterior surface of the stent, or both.

More specifically, the present invention relates to a covered stent device which is useful for supporting the walls of biliary ducts and for maintaining the patency of those ducts, and is relatively easily implanted at a desired location. The covering of the stent is substantially impermeable to body tissues and body fluids including liver bile. This attribute ensures that the covering is highly resistant to "wetting out" (i.e., transmural infiltration of fluid) by the bile fluid, and consequently will deter the initiation of biofilm formation. The covering reduces transmural bile permeability while simultaneously offering good flexibility, has a relatively thin wall for minimal interference with the volume of the duct passageway, and allows for a small delivery profile. In vitro testing has shown that a surface that is substantially non-porous with respect to liquid permeability, and more particularly to bacterial permeability, and has reduced luminal surface texture, will result in reduced bacterial attachment and colonization in comparison to materials with higher porosity and increased surface texture. It is believed that the use of a substantially non-porous covering will consequently reduce the incidence of occlusion due to bacterial biofilm formation. A further benefit of a substantially non-porous covering is that it can reduce the ingrowth and migration of malignant tissue through the stent covering and into the device lumen, thereby reducing the likelihood of occlusion due to tumor ingrowth or hyperplastic processes. In combination with the stent to which it is joined, the device is easily insertable in its small, collapsed state while being easily deployed to achieve a larger diameter for implantation. Once implanted at a desired site, it is intended to support the walls of the duct at the larger diameter and help maintain the patency of that portion of the duct.

By "substantially impermeable to liquids and bacteria" is meant that the covering is either entirely non-porous or has pores of only a relatively small size in order to be substantially impermeable to body tissues in the interest of precluding stent occlusion. A bubble point test is used to demonstrate this substantially impermeable character. As will be described below in further detail, the lumen of the tubular biliary stent is connected to a source of air pressure while being immersed in isopropyl alcohol. The covered stent (exclusive of any areas containing intentional perforations as further described below) should resist penetration by the luminal air pressure at 13 mm Hg±5% for a period of at least 30 seconds, penetration being indicated by air bubbles escaping from within the stent. More preferably, the covered stent should resist penetration by a pressure of 26 mm Hg, still more preferably by 39 mm Hg, and most preferably by 52 mm Hg.

Air bubbles escaping from the lumen of the covered stent beginning at 52 mm Hg pressure (as pressure is slowly increased to that value) are believed to be indicative of a largest aperture or pore through the covering having a smallest diameter of at least about 9 microns, according to conventional bubble point testing with isopropyl alcohol. Likewise, bubbles leaking beginning at the test pressure of about 13 mm Hg are believed to describe a largest aperture through the stent covering having a smallest diameter of about 35 microns, while 26 mm Hg corresponds to a largest aperture of about 18 microns, and a pressure of about 39 mm Hg would correspond to a largest aperture of about 12 microns.

The maximum known pressure within a biliary duct is about 40 mm Hg; therefore a device that is demonstrated to be impermeable to air leakage when tested at the most preferred pressure of 52 mm Hg has a substantial safety factor. However, in that absolute impermeability is not believed to be required for purposes of preventing occlusion by biological material, the lower pressure test value of 13 mm Hg is deemed to be appropriate as an indicator of adequate impermeability for effective biological performance.

While the impermeable stent covering may be made of various materials such as non-porous polypropylene films, the stent covering material is preferably comprised of a porous polymeric film that has been rendered impermeable by a polymeric coating. The use of porous precursor films (subsequently rendered impermeable) provides the stent covering with improved flexibility. A particularly preferred stent covering is porous expanded polytetrafluoroethylene (hereinafter ePTFE) which is made to be substantially impermeable to bile by the provision of a coating of a material which substantially seals the pores (void spaces) of the ePTFE. This composite covering material is biocompatible and very thin (less than about 0.4 mm thick and more preferably less than about 0.2 mm thick, 0.1 mm thick or 0.05 mm thick) and strong, offering good flexibility in a stent covered with the material. The thinness is a desirable attribute in that thinner walls allow for a smaller pre-deployment diameter for fitting into a delivery catheter of the smallest possible size. Further, following deployment and diametrical expansion, the thin walls of the device encroach less into the internal volume of the lumen of the device, which in turn aids in improved patency.

The material used for coating the ePTFE stent covering material is preferably fluorinated ethylene propylene (FEP) applied as will be described below. Alternative coating materials may also be used to substantially seal the pores of the ePTFE including perfluorinated alkoxy resins (PFA) and elastomeric materials such as silicones, polyurethanes and perfluorinated elastomers. Preferred coating materials are fluoropolymers because of the good biocompatibility of such materials. A variety of coating methods may be used including: spray coating, imbibing, lamination, powder mixing, powder coating, dispersion mixing, co-coagulation, co-extrusion, melt flow extrusion, draw extrusion and impregnation.

The stent covering may be beneficially provided to stent structures of various types including balloon expandable and self-expanding stents. A preferred stent material for use in the present invention is nitinol wire, which in combination with the covering material, allows for a covered stent that is relatively easily delivered percutaneously or endoscopically via a delivery catheter from which it is easily deployed and from which it may immediately self-expand following release of any diametrical restraining mechanism to fit tightly against the luminal surfaces of a bile duct. The stent may be provided with anchoring means on its exterior surface which aid in preventing migration of the stent from the location at which it is initially implanted. The thin wall construction of the covered stent allows it to be delivered with a relatively small diameter and consequently relatively flexible catheter, while allowing it to properly fit within a relatively large diameter body conduit following deployment. For example, the covered stent as described herein may be made to have an insertion diameter of about 10 French or even smaller, and delivered endoscopically from a 12 French or even smaller endoscope channel, and deployed to larger diameters of about 8 mm, 10 mm and 12 mm.

The flexibility of the preferred covering allows the resulting stent-graft to have good flexibility in bending, advantageous during insertion through tortuous passages and also of benefit in allowing the stent to be fitted to (deployed against) curved passageways. This flexibility reduces the risk of kinking of the covering material during bending of the material (or bending of the covered stent-graft).

The covered stent of the present invention may also be useful as a vascular stent wherein the thin, flexible, smooth and substantially liquid impermeable covering material may prove to be an effective vascular surface which avoids the accumulation of occlusive blood components on its luminal surface. Likewise, the stent of the present invention may be useful for other body conduits (e.g., esophagus, trachea, urethra, etc.) which may be narrowed or obstructed by malignant or benign strictures.

DETAILED DESCRIPTION OF THE DRAWINGS

Figure 1:
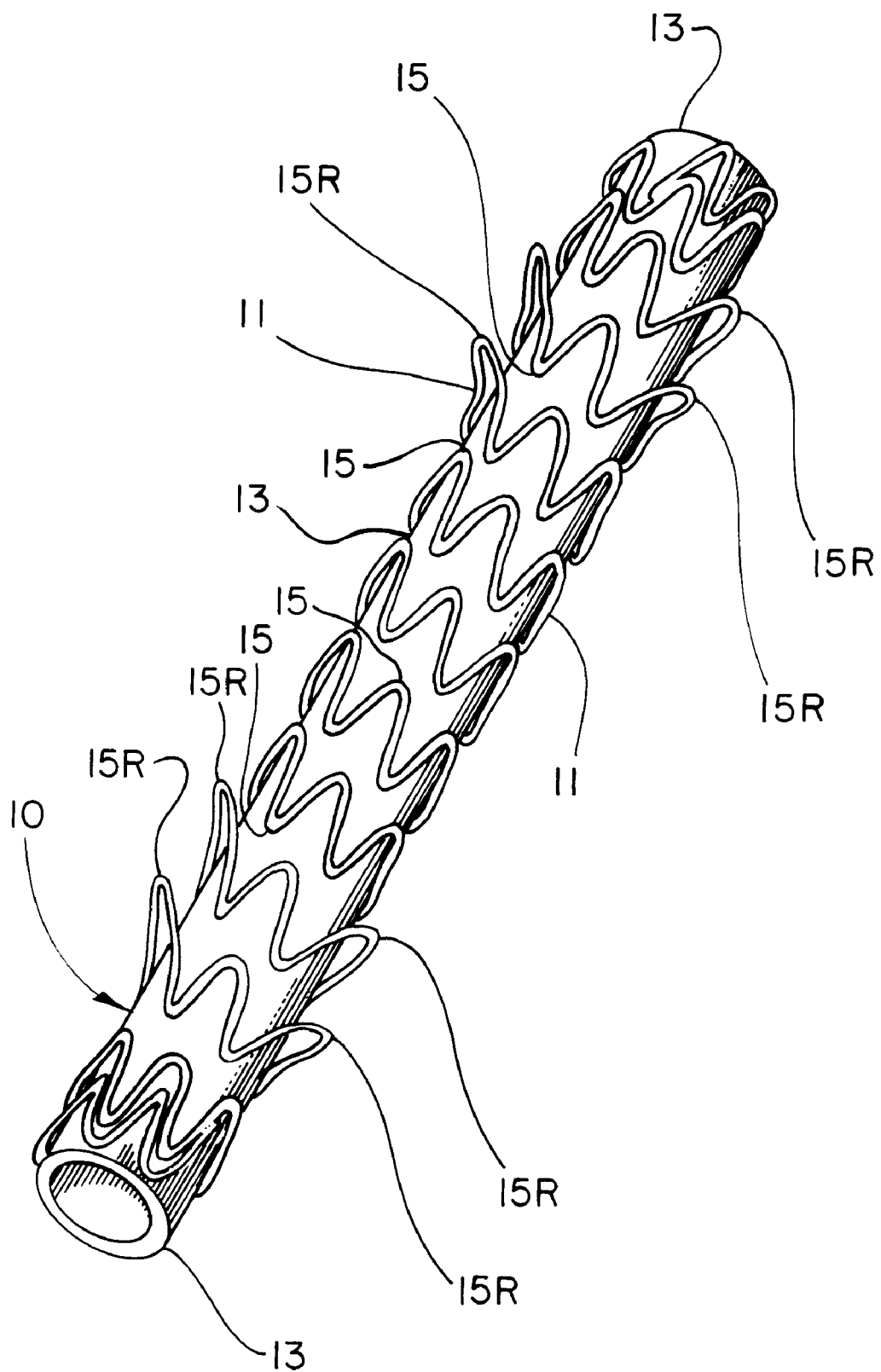
FIG. 1 is an isometric view of a covered stent of the present invention.

FIG. 1 shows the inventive covered stent 10 wherein a stent 11 is provided with a covering 13 of a thin, flexible material which is substantially impermeable to body fluids, particularly bile.

Figure 1A:
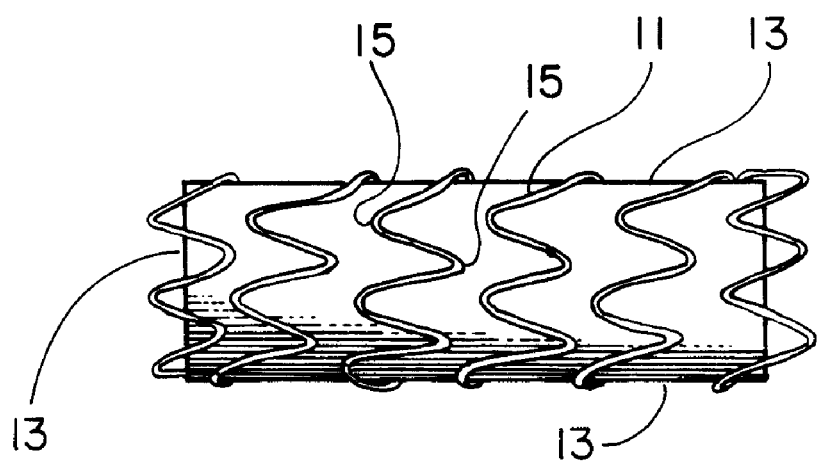
FIGS. 1A-1H are plan views of the covered stents of the present invention showing various ways that raised apices of the stents may be used to achieve different desired amounts of anchoring.
Figure 1B:
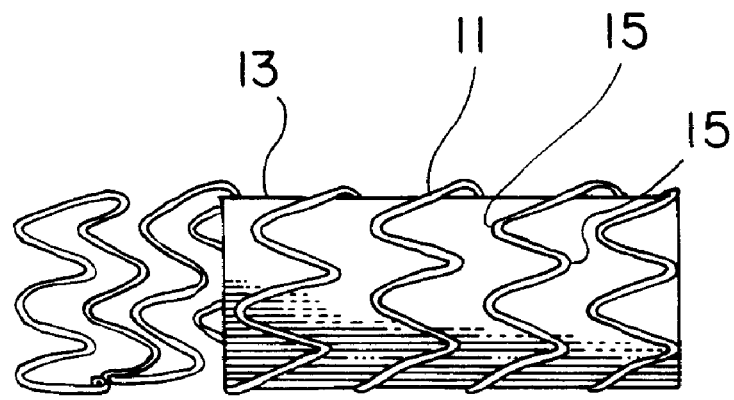
Figure 1C:
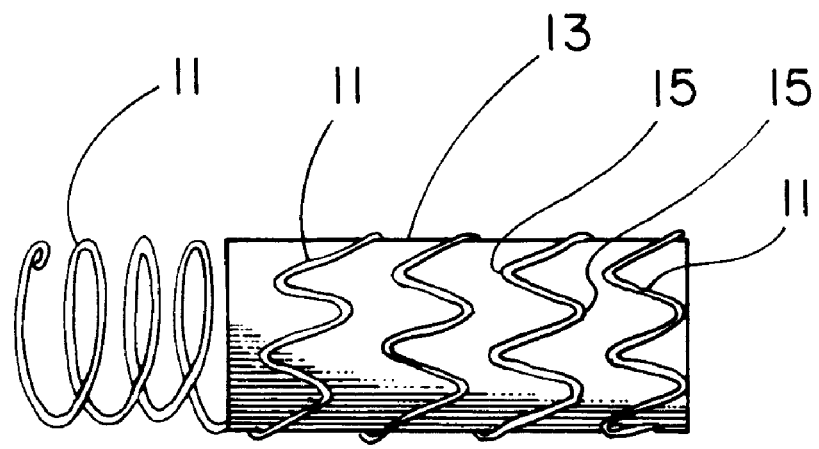
Figure 1D:
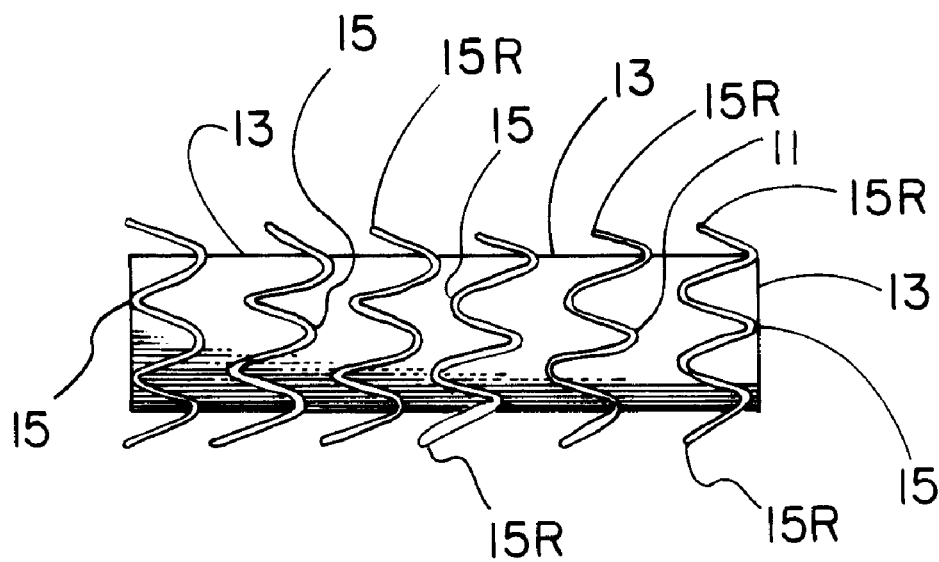
Figure 1E:
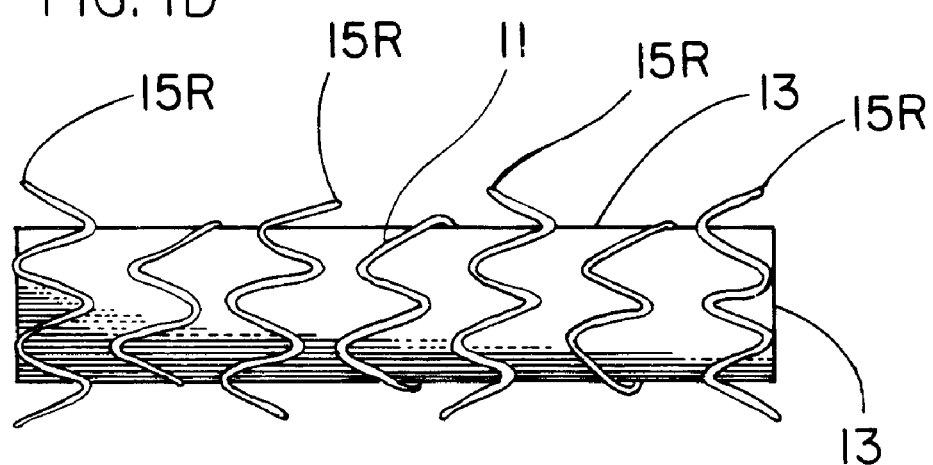
Figure 1F:
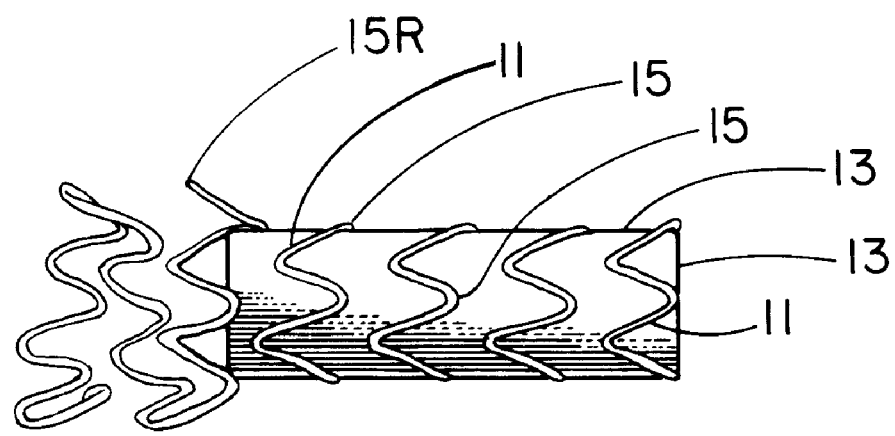
Figure 1G:
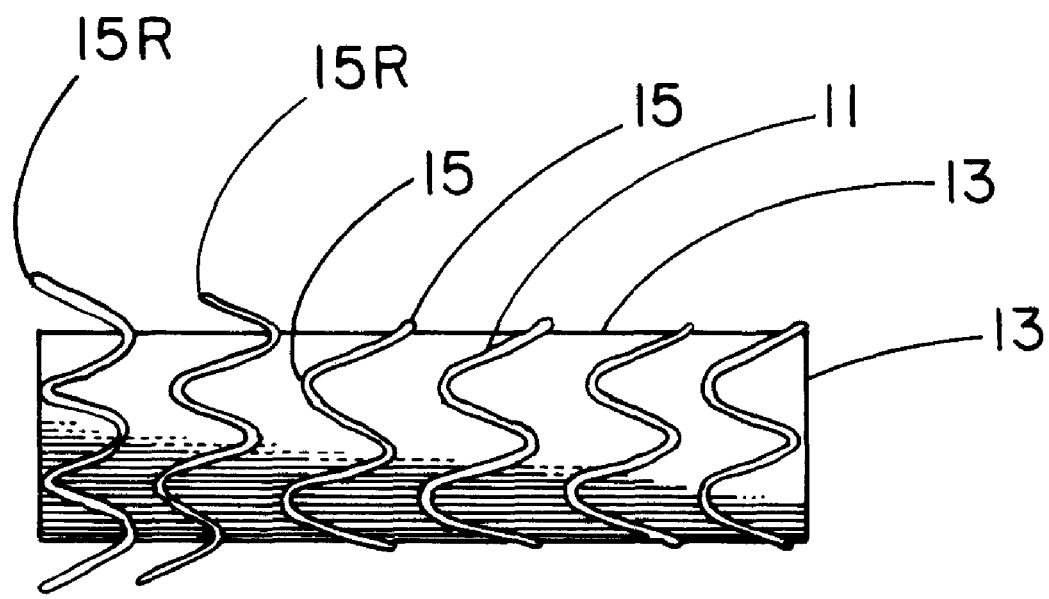
Figure 1H:
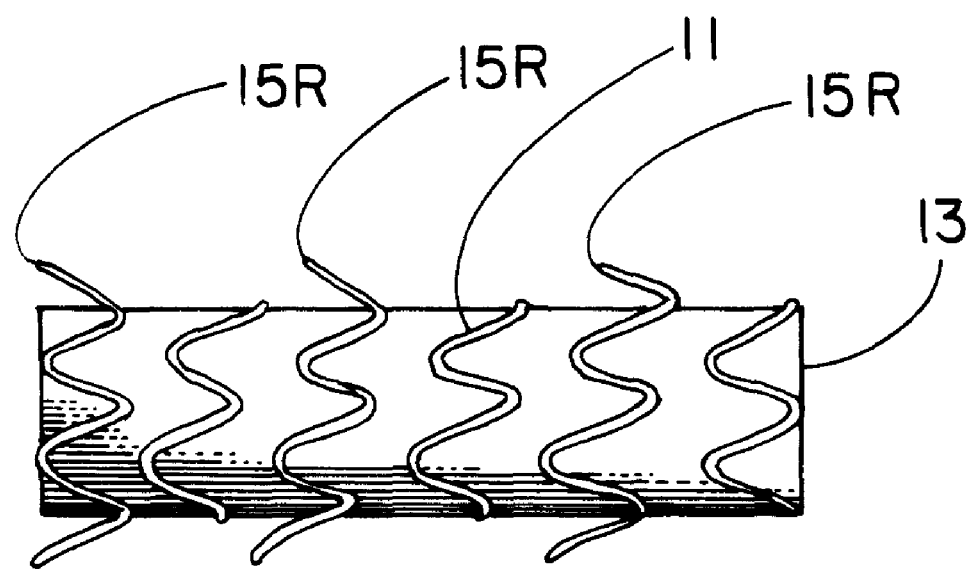

In the embodiment shown by FIG. 1, the stent 11 comprises wire which has been formed into a serpentine shape having apices 15, which shape is helically wound into a tubular form. The wire is preferably nitinol wire of, for example, about 0.23 mm diameter. A preferred nitinol wire is wire of this diameter which has been 45% cold worked and electropolished, available from Nitinol Devices & Components Inc., Fremont, Calif. Most preferably, the stent is formed from a single length of wire for simplicity and lowest possible profile, the ends of the wire being terminated by attaching to an adjacent serpentine winding. One method of forming the wire into the desired serpentine shape is to use a mandrel of similar diameter as the intended diameter of the desired tubular form of the stent. The mandrel is provided with appropriately located pins which protrude radially from the exterior surface of the mandrel in locations corresponding to the intended locations of the apices of the serpentine shape. A suitable length of the wire is then wrapped around the pins protruding from the mandrel surface creating the helically wound serpentine shape that results in the form of stent 10. Selected pins pertaining to raised apices described hereinbelow may be placed on appropriately elevated surfaces to achieve the desired amount of elevation. The general form of and method of making such a wire stent are described in WO 97/21403 (see, e.g., FIGS. 1A-2 of WO 97/21403 for the wire form which for purposes of the present invention does not require the additional coupling member 8 or linking member 20). This wire and mandrel assembly is placed into an oven set at 450° C. for about 15 minutes. Immediately following removal from the oven, the wire and mandrel assembly is quenched in water at about room temperature, following which the formed stent is removed from the mandrel.

The use of the serpentine winding of stent 11 shown in FIG. 1 allows the completed stent to be deployed with minimal foreshortening. The stent of the present invention when deployed from its small, insertion diameter to its largest, fully deployed diameter, will foreshorten less than about 10% of its insertion length. It is also capable of foreshortening less than about 8%, 6%, 4%, 2% or even 0% depending on construction details when properly deployed.

As also shown by FIG. 1, some of the apices 15 of the serpentine-wound wire may be raised above the tubular form so that they protrude somewhat above the outer surface of the remainder of the stent. These protruding or raised apices 15R may be useful as anchoring means for the covered stent in that they will protrude slightly into the wall of any body conduit into which the stent is implanted. In a preferred embodiment, the raised apices 15 are generally located at locations other than at the extreme ends of the stent; they are typically no closer than 1 mm to the ends of the stent. These raised apices are preferably formed during the forming of the stent wire (preferably nitinol wire and more preferably a single nitinol wire) into the desired helically wound, serpentine shape used for the stent.

It is apparent that there are a variety of ways of orienting the raised apices to achieve differing desired amounts of anchoring of the deployed stent. Variables include the angle of deviation of apices from parallel to the stent longitudinal axis, the height of raised apices, and whether all or any portion of particular apices are raised. The plan views of FIGS. 1A-1H show some of these ways which include raised apices all directed toward one end of the stent-graft, or directed to both ends of the stent-graft. They may all be located near one end, near both ends, only in the middle of the length or for substantially the entire length. It is generally preferred that raised apices alternate with adjacent apices which are not raised (i.e., adjacent on the same continuous section of stent wire) in the interest of providing a good bond between the stent and covering.

The attachment of the covering material to the stent may be accomplished by methods including those described by U.S. Pat. No. 5,735,892 to Myers et al., incorporated by reference herein. Mechanical attachment may be by methods such as by the use of sutures. The covering material will preferably be attached to the stent using an adhesive such as, for example, FEP which is effective as a meltable thermoplastic adhesive. It is apparent that a variety of adhesives may be used (including thermoset adhesives) as long as the adhesive chosen is adequately biocompatible. The adhesive may be applied to the stent in either solid (powdered) or liquid form by various methods including powder coating, dipping or spraying. Liquid forms may be diluted if desired with appropriate solvents as necessary for the chosen method of application. The adhesive-coated stent may be heated to ensure uniform coating of the stent by causing melting of the thermoplastic adhesive.

Alternatively, the coating material applied to the ePTFE film from which the stent covering is made may also be relied on for joining of the stent covering to the stent structure.

Figure 2:
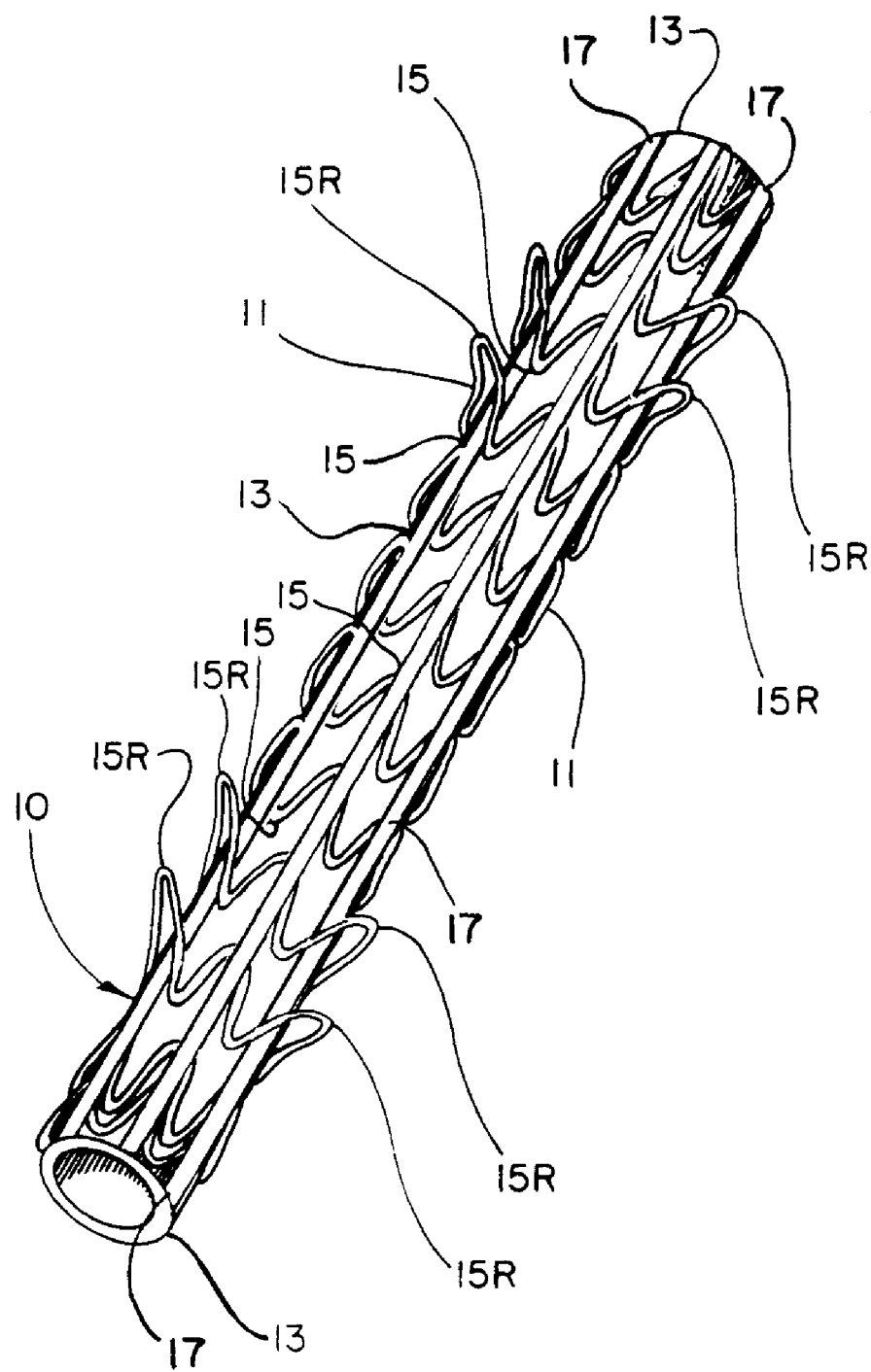
FIG. 2 is an isometric view of an alternative embodiment wherein adhesive strips are used to affix the stent to the covering.

In still another alternative shown in the isometric view of FIG. 2, the stent apices 15 may be secured to the stent covering 13 by one or more longitudinally oriented strips of material 17 which are adhered to the stent covering 13. A preferred material for the strips is the FEP-coated ePTFE film. The strips cover the apices 15 which are in contact with the stent covering 13 but do not cover the raised apices 15R, running instead under those apices 15R in order to avoid interfering with their raised character. It is apparent that the strips may be made to any desired width which is useful for the chosen stent dimensions and desired mechanical strength of the finished stent-graft.

Figure 3:
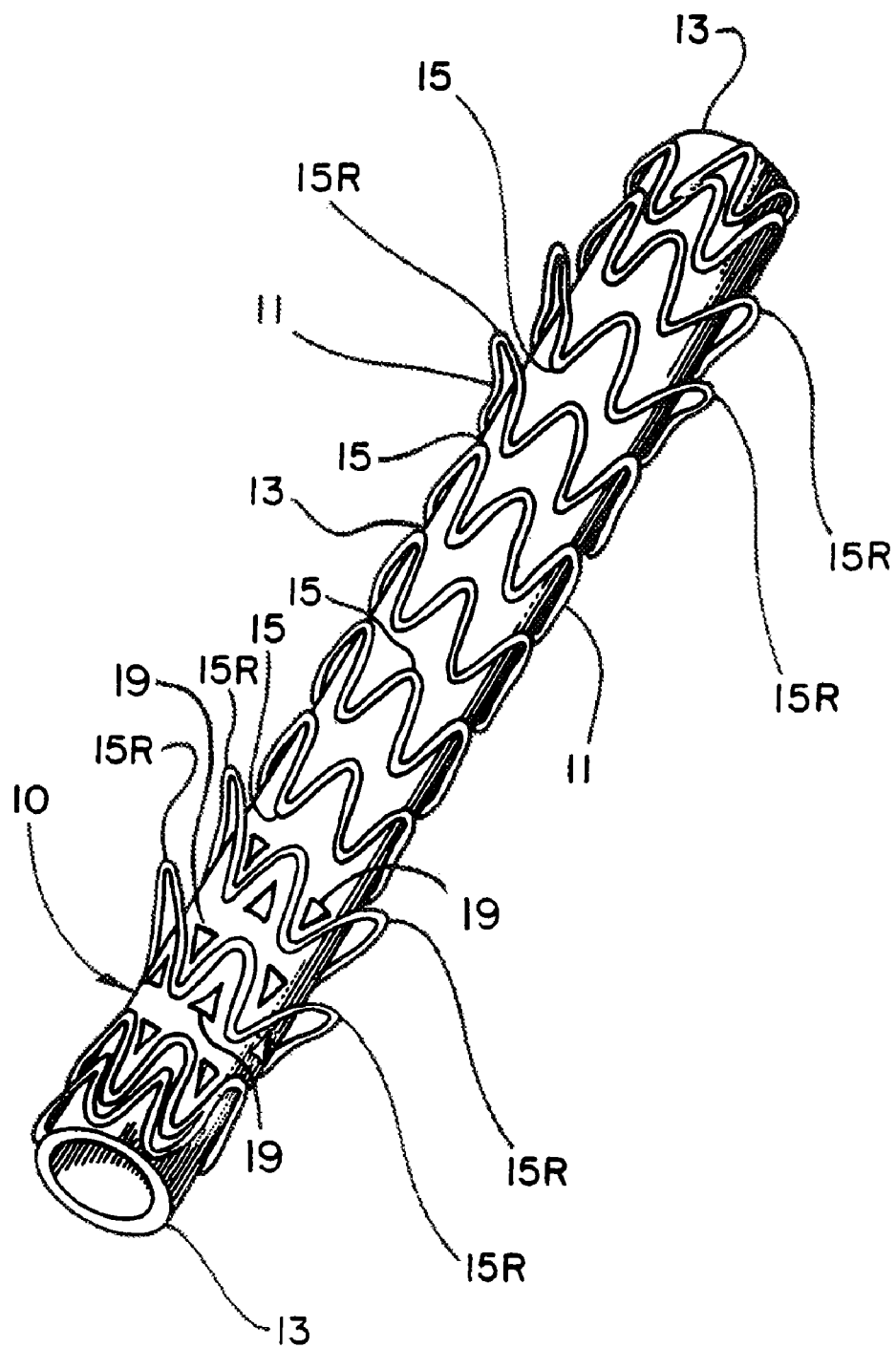
FIG. 3 is an isometric view of an alternative embodiment having macroscopic transluminal drainage openings through the stent covering.

FIG. 3 is an isometric view of an alternative embodiment having macroscopic transluminal drainage openings 19 through the stent covering 13. These may be utilized where it is desired to allow for local drainage (e.g., from branch ducts or side vessels) through the stent covering at specific sites. It is apparent that the openings may be provided in any desired shape, quantity or location through the stent covering. For example, circular openings of about 1.0 mm diameter may be conveniently provided between aligned stent apices 15. As shown by FIG. 3, triangular openings 19 are believed to be preferred for most situations as a triangular opening fits well between adjacent windings of the serpentine form. A preferred method of forming the openings through the stent covering is by the use of an appropriate laser.

Figure 4:
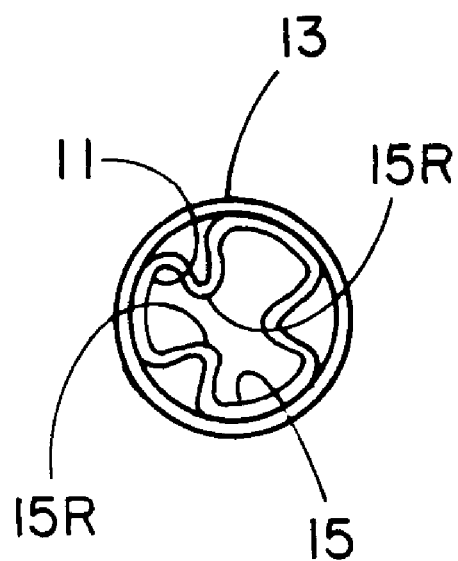
FIG. 4 is an end view of a stent of the present invention showing a stent having raised apices which extend into the lumen of the stent and providing a filtering capability as a result of protruding into the passageway.

FIG. 4 is an end view of a stent of the present invention showing a stent 11 having raised apices 15R which extend inwardly into the lumen of the stent 11 and provide a filtering capability as a result of protruding into the passageway. For biliary applications, such inwardly protruding apices would be beneficial for preventing retrograde flow of large particles such as food particles from the duodenum through the device and into the bile duct. Likewise, the device may also be useful blood vessel filters such as a vena cava filter.

Figure 5:
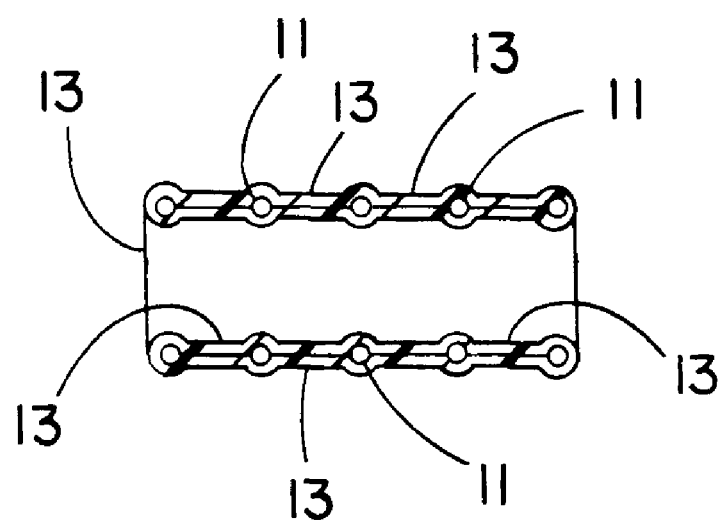
FIG. 5 shows a longitudinal cross section of a covered stent of the present invention wherein the stent covering is affixed to both the luminal and exterior surfaces of the stent.

FIG. 5 shows a longitudinal cross section of covered stents of the present invention wherein the stent covering 13 is affixed to both the luminal and exterior surfaces of the stent 11. The portion of the covering over the exterior of the stent may be interrupted if desired to allow for raised apices at desired locations.

The stent covering material is preferably, as noted above, an ePTFE film provided with a coating of FEP to seal the pores of the film. Films of ePTFE may be made as taught by U.S. Pat. Nos. 3,953,566 and 4,187,390. The FEP coating may be applied to the ePTFE film by a process which comprises the steps of:

a) contacting one side of the ePTFE film with a layer of FEP film (or another alternative thermoplastic polymer if so desired);
b) heating the composition obtained in step a) to a temperature above the melting point of the thermoplastic polymer;
c) stretching the heated composition of step b) while maintaining the temperature above the melting point of the thermoplastic polymer; and
d) cooling the product of step c).

The thermoplastic film coating applied to the ePTFE film by this method may be either continuous (non-porous) or discontinuous (porous). If discontinuous, the process may be adjusted to achieve the desired degree of porosity to include a coated film that is as porous as the precursor ePTFE film. The coated film used for the present invention is most preferably a continuously (non-porous or substantially non-porous) coated film. A precursor ePTFE film used to make the coated film for constructing the inventive stent devices has an average fibril length of about 50 microns and a bulk density of about 0.35 g/cc. Average fibril length was estimated from scanning electron photomicrographs of the surface of the ePTFE film. Thickness measurements were made (including for the determination of bulk volumes for density values) by placing a sample between the pads of a Mitutoyo model no. 804-10 snap gauge having a part no. 7300 frame and gently easing the pads into contact with the opposing surfaces of the sample under the full force of the spring-driven snap gauge pads. The FEP-coated film was of about 0.01 mm thickness.

Using this coated film, tubular stent coverings may be made by various methods. According to a preferred method, a stainless steel mandrel is helically wrapped with the film having the FEP coating facing away from the surface of the mandrel. An approximately 13 mm wide coated tape made from film of this type is used as a helical wrapping about a mandrel to form the tubular stent covering for the stent-graft of the present invention. One layer is applied by rotating the mandrel while paying film off onto the surface of the mandrel while traversing a supply spool of the film along a length of the mandrel until the desired length has been covered with a helically oriented wrapping of the film. The tapes are wrapped in a total of about three layers using a 50% overlap of adjacent edges of the wrapping. Adjacent edges of the helically wrapped film were overlapped by about 6.4 mm. Multiple passes traversing in either axial direction may also be employed to create additional helically-wrapped layers. The resulting helically-wrapped film tube may be optionally provided with another layer of the same film applied with a longitudinal orientation in the form of a "cigarette wrap" having a longitudinally seam of overlapped edges. The FEP-coated side of this layer of film again faces away from the surface of the mandrel. Finally, the film-wrapped mandrel is placed for a suitable period of time into an oven heated adequately to cause melting of the thermoplastic-coating in order to cause the adjacent layers of film to bond together to form a cohesive film-tube (e.g., about 20 minutes at 320° C.).

Following removal of the tubular stent covering and mandrel assembly from the oven, the ends of the stent covering are trimmed square (transverse to the longitudinal axis of the resulting film-tube) and to the desired length. It is apparent that the film-tube may be made to a length adequate to provide more than one stent covering. The ends may alternatively be trimmed following joining of the stent covering to the stent; if done in this manner the ends may be trimmed square or alternatively may follow the undulating form of the end of the stent wire.

The previously formed stent (preferably adhesive-coated as described above) is then carefully fitted over the stent covering which is still on the mandrel. If it is desired to temporarily secure the stent to the covering prior to further construction, the stent covering may be tacked to the stent at various locations using a locally applied heat source such as a clean soldering iron.

FIG. 1 shows the stent component with the apices of adjacent windings in alignment with each other with respect to the longitudinal axis of the covered stent device. This is preferred for improved handling and bending properties of the device. The "tacking" procedure, if done following positioning of the stent apices to properly align them, is a means of ensuring alignment of the apices during any subsequent manufacturing steps.

The stent may be permanently joined to the stent covering by a variety of means. The above-described tacking method may be adequate at a minimum. More preferably, additional ePTFE film having the FEP coating is applied either by radial or circumferential wrapping with the FEP coating facing toward the stent and mandrel. Longitudinal strips of the FEP-coated film (FIG. 2), again with the FEP coating facing inward, may be first placed along the length of the covered-stent and mandrel assembly prior to helical or circumferential wrapping if desired to further secure the stent to the underlying covering and impart increased longitudinal strength. It is apparent that any protruding stent apices intended as stent anchoring means should not be covered by any exteriorly placed film. Finally, the assembly is heated appropriately to cause melting of the thermoplastic material (e.g., the FEP film coating) to attach together the various components of the device. Following heating and subsequent cooling, the device is removed from the mandrel. While this method of joining the stent and covering is preferred, it is apparent that other methods such as, for example, solvent welding, may be utilized as well.

Figure 6A:
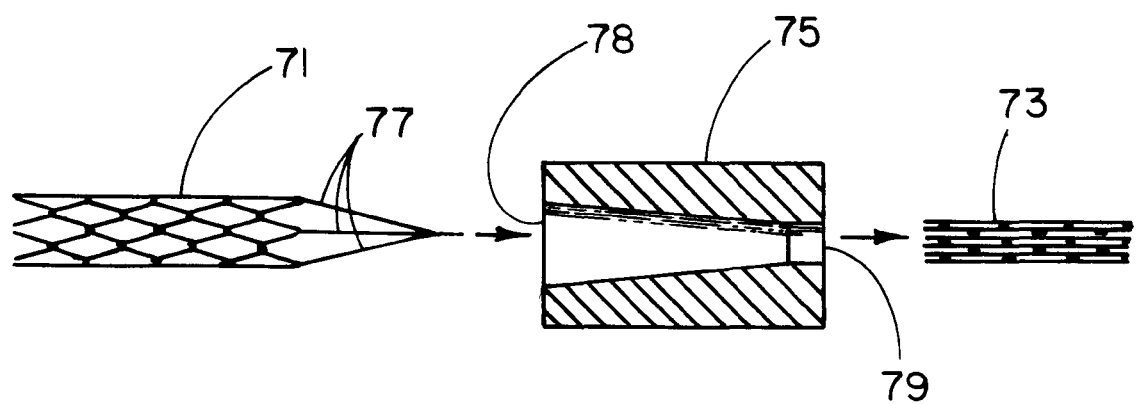
FIGS. 6A and 6B describe apparatus useful in the manufacture of the stent-graft of the present invention.
Figure 6B:
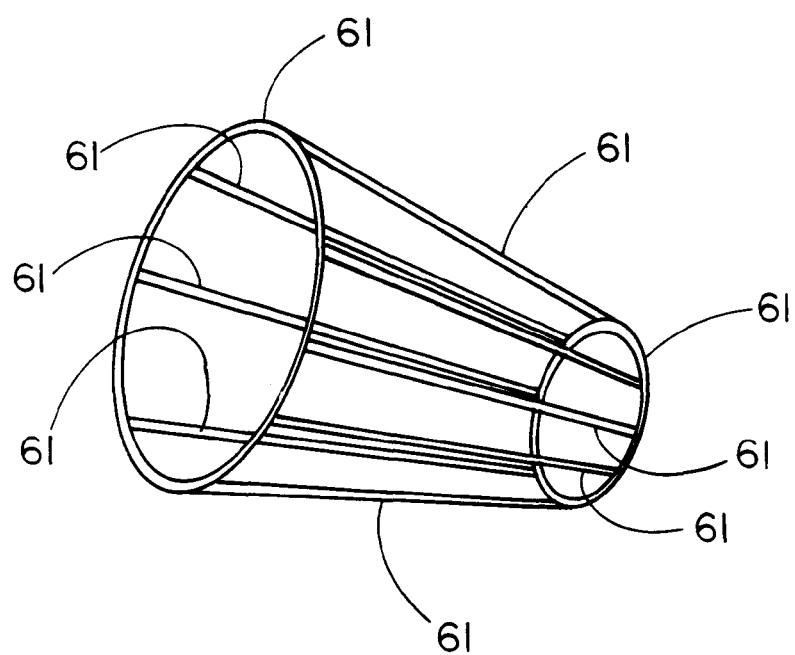

The covering is preferably applied to the stent at the largest diameter of the stent (i.e., the fully deployed diameter). The device may then be diametrically compressed by any of various means to allow insertion into or onto the distal end of a catheter from which it will subsequently be deployed following insertion of the catheter into a body conduit for implantation at a desired location. Diametrical compression of the stent device may be accomplished by various means including means described by U.S. Pat. No. 5,735,892 to Myers et al. FIG. 6A shows a tapered die described by Myers et al. that is particularly useful, wherein the stent at its deployed diameter 71 (covering not shown for clarity) is inserted into the large diameter orifice 78 of die 75 and pulled through die 75 using temporary cords 77. The stent 73 exits the small orifice 79 of the die at its smaller, compressed diameter as appropriate for insertion into a patients vessel for passage to the desired implant site. Rather than use a solid, one-piece die as shown by FIG. 6A, the die may be made from several wire elements 61 as shown by the isometric view of FIG. 6B. The use of individual wires 61 may be used to guide the apices of the stent during passage of the stent toward the smaller opening of the die and to reduce the force needed to draw the stent through the die. In another alternative, the wire form may be used within the tapered lumen of the die as an axial guide, or the lumen of the die may be provided with grooves. Other methods of diametrically compressing a self expanding nitinol stent include (but are not limited to): inducing a martensitic phase through the use of refrigerant, pulling the device through a tapered die, rolling, and true radial crush through the use of devices such as iris diaphragms. Factors which contribute to the decision of which diametrical compression method is implemented include the hoop strength of the stent structure and the specific stent configuration of the chosen stent structural elements (e.g., a serpentine wire oriented in a helical configuration about the longitudinal axis of the stent with raised apices in a specific pattern).

It is apparent that the inventive stent may be provided with additional features or coatings known to those of skill in the art. For example, the device may be made to be radiopaque or may be coated or impregnated with any of a variety of therapeutic, anti-microbial or preservative agents which might be beneficially delivered to the implantation site.

Bubble point testing is deemed to be an appropriate method to evaluate the substantially impermeable character of the covered stent. This type of test is described generally by ASTM F316-86. That methodology is modified to the extent described herein below in order to test a tubular device rather than a flat sheet membrane.

In the evaluation of film or membrane porosity using a bubble point test, liquids with surface free energies less than that of ePTFE can be forced out of the structure with the application of a differential pressure. This clearing of the liquid will occur from the largest passageways first. A passageway is then created through which bulk air flow can take place. The air flow appears as a steady stream of small bubbles through the liquid layer on top of the sample. The pressure at which the first bulk air flow takes place is called the bubble point and is dependent on the surface tension of the test fluid and the size of the largest opening. The bubble point can be used as a relative measure of the structure of a membrane and the size of the largest opening or pore through the membrane, and is often correlated with some other type of performance criteria such as filtration efficiency.

Figure 7:
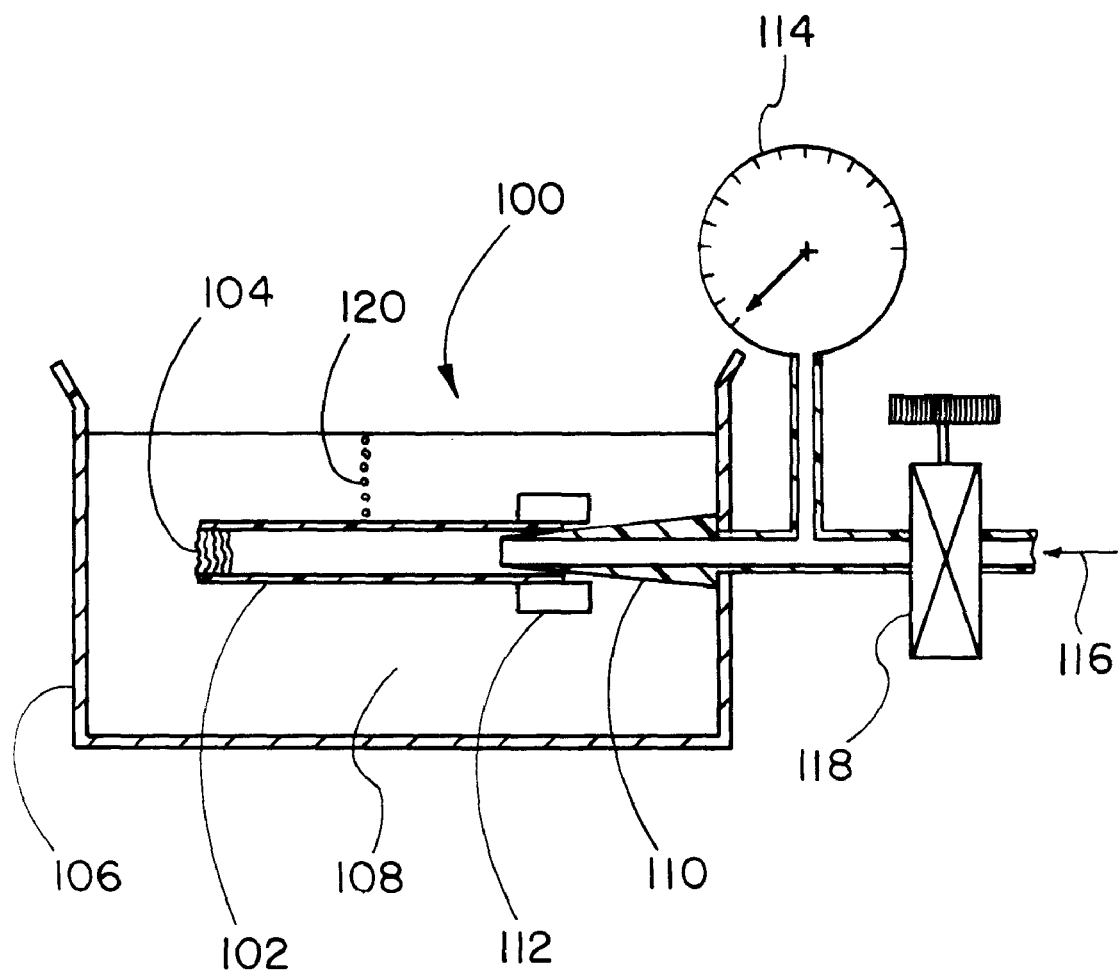
FIG. 7 describes a bubble point test apparatus for evaluation of the substantially impermeable character of the stent-graft of the present invention.

A low-pressure bubble point test is described in FIG. 7. Shown is a test fixture 100 used to determine a bubble point for a typical tubular device. The device 102 is prepared for testing by sealing one end 104. Adhesives can be used, with or without a plug, to effectively seal the end. After one end of the device is sealed, the device is positioned into a test tank 106, filled with isopropyl alcohol 108. The device 102 is then positioned onto a tapered air pressure inlet 110. The device can be secured to the tapered air pressure inlet by a friction fit collar 112 to ensure that a tight, leak-free seal is obtained. The tapered air pressure inlet 110 is connected to a precision air pressure gage or mercury manometer. An air pressure supply 116 is then connected to a pressure regulator 118.

To begin the test, the pressure regulator is slowly opened (or adjusted up from zero pressure) until the desired pressure is reflected by the precision gage or manometer. The desired pressure, that is, the test pressure deemed appropriate to indicate substantial impermeability or lack thereof (e.g., 13 mm Hg, or 26 mm Hg, or 39 mm Hg, or 52 mm Hg as described previously above, all ±5%), is maintained for approximately 30 seconds, during which time the device under test 102 is observed under a magnification of about 1.75×. A stream of bubbles escaping from within the covered stent indicates a lack of substantial impermeability at that test pressure.

If the device is deemed to be substantially impermeable, the bubble point of the device, i.e., the pressure at which the device begins to leak air at the largest opening through the device wall, can be determined by a gradual further increasing of the air pressure until the continuous stream of bubbles 120 does appear. The bubble point pressure is then reflected on the pressure gage or manometer. The higher the pressure required for leakage, the smaller the pore size of the pore that is responsible for the leak. Bubble streams emanating from the end seal 104 or from the portion attached to the tapered air pressure inlet 110 invalidate the test results. Only portions of a device devoid of intentional macroscopic openings should be tested. All tests described herein were performed on devices of the present invention at an altitude of about 2100 meters above sea level and at ambient temperature.

While particular embodiments of the present invention have been illustrated and described herein, the present invention should not be limited to such illustrations and descriptions. It should be apparent that changes and modifications may be incorporated and embodied as part of the present invention within the scope of the following claims.

We claim:

1. An endoprosthesis for use in supporting a body conduit, said device comprising
   a stent having structural elements arranged in a generally tubular form and interstices between adjacent structural elements,
   said stent having a first diameter prior to implantation and a second diameter following implantation wherein said first diameter is smaller than said second diameter,
   said stent being provided with a covering over at least a portion of said structural elements, said covering having a thickness extending between inner and outer surfaces of the covering,
   wherein the covering comprises a material which is substantially liquid impermeable,
   wherein a multiplicity of macroscopic openings are provided through the thickness of the covering, and
   wherein one or more of said structural elements provide protruding means extending beyond the generally tubular form for anchoring said stent to said body conduit.

2. An endoprosthesis according to claim 1 wherein the stent is a balloon expandable stent.

3. An endoprosthesis according to claim 1 wherein the stent is a self expanding stent.

4. An endoprosthesis according to claim 1 wherein the stent is a nitinol stent.

5. An endoprosthesis according to claim 4 wherein the stent is nitinol wire.

6. An endoprosthesis according to claim 5 wherein the stent comprises nitinol wire formed into a serpentine pattern which is helically wrapped into the tubular form.

7. An endoprosthesis according to claim 6 wherein the nitinol is a single nitinol wire.

8. An endoprosthesis according to claim 6 wherein one or more apices of the serpentine pattern protrude inwardly from the tubular form.

9. An endoprosthesis according to claim 6 wherein the anchoring means comprise one or more apices of the serpentine pattern which are formed to outwardly protrude beyond the tubular form.

10. An endoprosthesis according to claim 9 wherein the anchoring means comprise one or more outwardly protruding apices which are formed from a wire that is continuous with other apices that do not protrude outwardly beyond the tubular form.

11. An endoprosthesis according to claim 1 wherein the covering is a porous material rendered non-porous or substantially non-porous by a coating.

12. An endoprosthesis according to claim 11 wherein the covering is rendered substantially impermeable to body fluids by a coating process selected from the group consisting of spray coating, imbibing, lamination, powder mixing, powder coating, dispersion mixing, co-coagulation, co-extrusion, melt flow extrusion, draw extrusion and impregnation.

13. An endoprosthesis according to claim 11 wherein the covering is porous expanded polytetrafluoroethylene.

14. An endoprosthesis according to claim 12 wherein the porous expanded polytetrafluoroethylene is rendered non-porous or substantially non-porous by a thermoplastic fluoropolymer coating.

15. An endoprosthesis according to claim 12 wherein the thermoplastic fluoropolymer is fluorinated ethylene propylene.

16. An endoprosthesis according to claim 1 wherein the covering is joined to the stent with an adhesive.

17. An endoprosthesis according to claim 16 wherein the adhesive is a thermoplastic adhesive.

18. An endoprosthesis according to claim 17 wherein the thermoplastic adhesive is a fluoropolymer.

19. An endoprosthesis according to claim 18 wherein the fluoropolymer is fluorinated ethylene propylene.

20. An endoprosthesis according to claim 1 wherein said stent foreshortens less than about 10 percent of its length at its first diameter when deployed to the second diameter.

21. An endoprosthesis according to claim 1 wherein the macroscopic openings are triangular in shape.

22. An endoprosthesis according to claim 1 wherein the covering is less than about 0.4 mm thick.

23. An endoprosthesis according to claim 1 wherein the covering is less than about 0.2 mm thick.

24. An endoprosthesis according to claim 23 wherein the anchoring means comprise one or more apices of the serpentine pattern which are formed to outwardly protrude beyond the tubular form.

25. An endoprosthesis according to claim 1 wherein the covering is less than about 0.1 mm thick.

26. An endoprosthesis according to claim 1 wherein the covering is less than about 0.05 mm thick.

27. An endoprosthesis according to claim 1 wherein longitudinally oriented strips are affixed to the covering.

28. An endoprosthesis according to claim 26 wherein the longitudinally oriented strips attach the stent to the covering.

29. An endoprosthesis according to claim 1 wherein substantially liquid impermeable is indicated by no air leakage during a bubble point test at a pressure of about 13 mm Hg.

30. An endoprosthesis according to claim 1 wherein substantially liquid impermeable is indicated by no air leakage during a bubble point test at a pressure of about 26 mm Hg.

31. An endoprosthesis according to claim 1 wherein substantially liquid impermeable is indicated by no air leakage during a bubble point test at a pressure of about 39 mm Hg.

32. An endoprosthesis according to claim 1 wherein substantially liquid impermeable is indicated by no air leakage during a bubble point test at a pressure of about 52 mm Hg.

33. An endoprosthesis according to claim 1 wherein longitudinally oriented strips are affixed to the covering.

34. An endoprosthesis according to claim 33 wherein the longitudinally oriented strips attach the covering to the stent.

35. An endoprosthesis for use in supporting a body conduit,
said device comprising a stent having a generally tubular form,
said stent having structural elements and interstices between adjacent structural elements,
said stent being provided with a covering over at least a portion of said structural elements, said covering having a thickness extending between inner and outer surfaces of the covering,
wherein the covering comprises a material which is substantially liquid impermeable,
wherein said stent comprises a single wire,
wherein a multiplicity of macroscopic openings are provided through the thickness of the covering, and
wherein one or more of said structural elements provide protruding means extending beyond the generally tubular form for anchoring said stent to said body conduit.

36. An endoprosthesis according to claim 35 wherein the wire comprises nitinol wire.

37. An endoprosthesis according to claim 35 wherein said single wire is formed into a serpentine pattern having apices wherein one or more apices of the serpentine pattern protrude inwardly from the tubular form.

38. An endoprosthesis according to claim 35 wherein the covering comprises porous expanded polytetrafluoroethylene.

39. An endoprosthesis according to claim 38 wherein the porous expanded polytetrafluoroethylene is rendered non-porous or substantially non-porous with a coating of fluorinated ethylene propylene.

40. An endoprosthesis according to claim 35 wherein the covering is joined to the stent with an adhesive.

41. An endoprosthesis according to claim 40 wherein the adhesive is fluorinated ethylene propylene.

42. An endoprosthesis according to claim 35 wherein substantially liquid impermeable is indicated by no air leakage during a bubble point test at a pressure of about 13 mm Hg.

43. An endoprosthesis according to claim 35 wherein substantially liquid impermeable is indicated by no air leakage during a bubble point test at a pressure of about 26 mm Hg.

44. An endoprosthesis according to claim 35 wherein substantially liquid impermeable is indicated by no air leakage during a bubble point test at a pressure of about 39 mm Hg.

45. An endoprosthesis according to claim 35 wherein substantially liquid impermeable is indicated by no air leakage during a bubble point test at a pressure of about 52 mm Hg.

* * * * *